US012606507B2

(12) United States Patent
Wiederhold et al.

(10) Patent No.: US 12,606,507 B2
(45) Date of Patent: Apr. 21, 2026

(54) METHOD FOR THE PREPARATION OF 1,2-PROPANEDIOL

(71) Applicant: Evonik Operations GmbH, Essen (DE)

(72) Inventors: Holger Wiederhold, Darmstadt (DE); David Bolz, Frankfurt (DE); Jürgen Glenneberg, Offenbach (DE)

(73) Assignee: Evonik Operations GmbH, Essen (DE)

( * ) Notice: Subject to any disclaimer, the term of this patent is extended or adjusted under 35 U.S.C. 154(b) by 497 days.

(21) Appl. No.: 18/249,825

(22) PCT Filed: Oct. 7, 2021

(86) PCT No.: PCT/EP2021/077756

§ 371 (c)(1),
(2) Date: Apr. 20, 2023

(87) PCT Pub. No.: WO2022/084061

PCT Pub. Date: Apr. 28, 2022

(65) Prior Publication Data

US 2023/0399279 A1     Dec. 14, 2023

(30) Foreign Application Priority Data

Oct. 21, 2020    (EP) ..................................... 20203065

(51) Int. Cl.

| | |
|---|---|
| *C07C 29/48* | (2006.01) |
| *B01D 3/14* | (2006.01) |
| *B01J 23/42* | (2006.01) |
| *B01J 31/02* | (2006.01) |
| *C07C 29/80* | (2006.01) |

(52) U.S. Cl.

CPC .............. *C07C 29/48* (2013.01); *B01D 3/143* (2013.01); *B01J 23/42* (2013.01); *B01J 31/0255* (2013.01); *C07C 29/80* (2013.01)

(58) Field of Classification Search

CPC ......... C07C 29/48; C07C 29/80; B01D 3/143; B01J 23/42; B01J 31/0255

See application file for complete search history.

(56) References Cited

U.S. PATENT DOCUMENTS

| | | | |
|---|---|---|---|
| 4,308,409 A | 12/1981 | Wu et al. | |
| 10,214,471 B2 | 2/2019 | Wiederhold et al. | |
| 2004/0094478 A1* | 5/2004 | Nobel .................... | B01D 11/00 |
| | | | 210/634 |
| 2018/0354878 A1 | 12/2018 | Wiederhold et al. | |

FOREIGN PATENT DOCUMENTS

| | | | |
|---|---|---|---|
| CN | 108623457 A | * | 10/2018 |
| CN | 108779053 A | | 11/2018 |
| WO | 2017/089075 | | 6/2017 |

OTHER PUBLICATIONS

CN108623457A (Zhao et al.; English language machine translation) (Year: 2018).*
("Propanediols" in Ullman's Encyclopedia of Industrial Chemistry, 2018, pp. 1-15 (Sullivan et al.) (Year: 2018).*
International Search Report issued Dec. 20, 2021, in PCT/EP2021/077756, 5 pages.
Written Opinion issued Dec. 20, 2021, in PCT/EP2021/077756, 7 pages.
U.S. Appl. No. 18/249,984, filed Apr. 21, 2023, Wiederhold et al.
U.S. Appl. No. 18/249,724, filed Apr. 19, 2023, Wiederhold et al.
U.S. Appl. No. 18/249,980, filed Apr. 21, 2023, Wiederhold et al.
U.S. Appl. No. 18/249,584, filed Apr. 19, 2023, Wiederhold et al.
U.S. Appl. No. 18/249,695, filed Apr. 19, 2023, Wiederhold et al.
U.S. Appl. No. 18/249,729, filed Apr. 19, 2023, Bolz et al.

(Continued)

*Primary Examiner* — Amy C Bonaparte
*Assistant Examiner* — Derek Rhoades
(74) *Attorney, Agent, or Firm* — Grüneberg Global IP, PLLC

(57)     ABSTRACT

A method for preparing 1,2-propanediol involves reacting propene with hydrogen peroxide in the presence of a catalyst mixture, containing a phase transfer catalyst and a heteropolytungstate, in a liquid reaction mixture containing an aqueous phase with a maximum apparent pH of 6 and an organic phase. The method then involves separating the reaction mixture into an aqueous phase ($P_a$) containing 1,2-propanediol and formic acid and an organic phase ($P_o$); recycling at least part of the separated organic phase ($P_o$) to the reaction; contacting at least a part of the separated aqueous phase ($P_a$) with a palladium catalyst; and recovering 1,2 propanediol from the aqueous phase provided by the contacting. The contacting of at least a part of the separated aqueous phase ($P_a$) with the palladium catalyst reduces the content of formic acid.

15 Claims, No Drawings

(56) References Cited

OTHER PUBLICATIONS

U.S. Appl. No. 18/249,908, filed Apr. 20, 2023, Wiederhold et al.
U.S. Appl. No. 18/249,982, filed Apr. 21, 2023, Wiederhold et al.
U.S. Appl. No. 18/249,660, filed Apr. 19, 2023, Wiederhold et al.
U.S. Appl. No. 18/249,906, filed Apr. 20, 2023, Wiederhold et al.
D.M. Ruthven, et al., "The Catalytic Decomposition of Aqueous Formic Acid over Suspended Palladium Catalysts", Journal of Catalysis 21, 1971, pp. 39-47.
Indian Office Action dated Jul. 7, 2023, in Indian Application No. 202347034233, with English translation, 6 pages.

* cited by examiner

METHOD FOR THE PREPARATION OF 1,2-PROPANEDIOL

CROSS-REFERENCE TO RELATED APPLICATIONS

This application is a National Stage entry under § 371 of International Application No. PCT/EP2021/077756, filed on Oct. 7, 2021, and which claims the benefit of priority to European Application No. 20203065.6, filed on Oct. 21, 2020. The content of each of these applications is hereby incorporated by reference in its entirety.

BACKGROUND OF THE INVENTION

Field of the Invention

The present invention relates to a method for the preparation of 1,2-propanediol by reacting propene with hydrogen peroxide.

Description of Related Art

In a well-established process used in the industry, 1,2-propanediol is prepared by reacting propene oxide with water. Propene oxide can be made on an industrial basis using the HPPO process comprising the reaction of propene with hydrogen peroxide in the presence of a titanium zeolite catalyst and an organic solvent. Propene oxide is then isolated and purified prior to the step of reacting it with water to make 1,2-propanediol.

WO 2017/089075 discloses a method for producing 1,2-propanediol from propene and hydrogen peroxide comprising: a) reacting propene with hydrogen peroxide in the presence of a catalyst mixture comprising a phase transfer catalyst and a heteropolytungstate, wherein the reaction is carried out in a liquid mixture comprising an aqueous phase with a maximum pH of 6 and an organic phase, b) dividing the two-phase mixture from step a) into an aqueous phase and an organic phase containing propylene oxide, c) returning the propylene oxide contained in the separated organic phase into the reaction from step a) and d) separating 1,2-propanediol from the aqueous phase separated in step b).

In the method described in WO 2017/089075, formic acid is formed in reaction step a) in a side reaction by cleavage of 1,2-propanediol to formaldehyde and acetaldehyde and subsequent oxidation of formaldehyde to formic acid. Formic acid will be in the aqueous phase and may lead to corrosion problems in subsequent high temperature work-up steps such as in distillation steps for recovering 1,2-propanediol (MPG) and other valuable products like dipropylene glycol (DPG) and tripropylene glycol (TPG). Thus, it is an object of the present invention to provide a method for the preparation of 1,2-propanediol wherein corrosion problems in subsequent distillation steps for recovering the valuable products are mitigated.

SUMMARY OF THE INVENTION

The inventor of the present invention has now found that formic acid formed as a by-product can be decomposed by contacting aqueous phase (Pa) separated from the reaction mixture with a palladium catalyst and that carrying out such contacting step can reduce corrosion problems in a subsequent step of recovering 1,2-propanediol.

Subject of the invention is therefore a method for the preparation of 1,2-propanediol comprising:

a) reacting propene with hydrogen peroxide in the presence of a catalyst mixture comprising a phase transfer catalyst, phosphoric acid and a heteropolytungstate in a liquid reaction mixture comprising an aqueous phase with a maximum apparent pH of 6 and an organic phase, herein the term "apparent pH" here refers to a value determined by measurement with a glass electrode employing a commercial pH meter calibrated with aqueous buffer solutions of known pH for measuring dilute aqueous solutions;

b) separating the reaction mixture into an aqueous phase ($P_a$) comprising 1,2-propanediol and formic acid and an organic phase ($P_o$);

c) recycling at least a part of the separated organic phase ($P_o$) to the reaction step a);

d) contacting at least a part of the aqueous phase (Pa) separated in step b) with a palladium catalyst to provide a treated aqueous phase, wherein no hydrogen is added in contacting step d); and e) recovering 1,2-propanediol from the treated aqueous phase provided in step d).

In a further aspect the present invention relates to the use of a contacting step d) to decompose formic acid in a method for the preparation of 1,2-propanediol comprising:

a) reacting propene with hydrogen peroxide in the presence of a catalyst mixture comprising a phase transfer catalyst, phosphoric acid and a heteropolytungstate in a liquid reaction mixture comprising an aqueous phase with a maximum apparent pH of 6 and an organic phase, wherein the term "apparent pH" here refers to a value determined by measurement with a glass electrode employing a commercial pH meter calibrated with aqueous buffer solutions of known pH for measuring dilute aqueous solutions;

b) separating the reaction mixture into an aqueous phase (Pa) comprising 1,2-propanediol and formic acid and an organic phase (Po);

c) recycling at least a part of the separated organic phase (Po) to the reaction step a);

d) contacting at least a part of the aqueous phase (Pa) separated in step b) with a palladium catalyst to provide a treated aqueous phase; and e) recovering 1,2-propanediol from the treated aqueous phase provided in step d).

DETAILED DESCRIPTION OF THE INVENTION

In the method of the present invention, propene is reacted in a step a) with hydrogen peroxide in the presence of a catalyst mixture comprising a phase transfer catalyst and a heteropolytungstate. This reaction is carried out in a liquid reaction mixture which comprises an aqueous phase with a maximum apparent pH of 6 and an organic phase.

Propene can be used in pure form or in a mixture with propane, wherein the proportion of propane may be up to 20 mol-%. The proportion of propane in the propene used is preferably less than 5 mol-%. Propene is preferably employed in a molar excess to hydrogen peroxide, preferably in a molar ratio of propene to hydrogen peroxide of from 1.1:1 to 10:1.

Hydrogen peroxide is preferably used in the form of an aqueous solution, preferably with a hydrogen peroxide content of 10 to 80% by weight, particularly preferably 30 to 70% by weight. Any commercially available grade of aqueous hydrogen peroxide solutions can be used. A crude hydrogen peroxide product obtained in the extraction stage of the anthraquinone process for producing hydrogen peroxide may also be used.

The catalyst mixture used in step a) comprises a heteropolytungstate. The heteroatom is preferably phosphorus or arsenic and is particularly preferably phosphorus, i.e. the heteropolytungstate is particularly preferably a polytungstophosphate. Heteropolytungstates are well known to a person skilled in the art. Preferred polytungstophosphates have a molar ratio of phosphorus to tungsten in the range of from 1:2 to 1:12. The polytungstophosphate is preferably generated in situ by combining phosphoric acid and sodium tungstate, which can be carried out in the liquid reaction mixture itself or prior to adding the polytungstophosphate to the liquid reaction mixture. Phosphoric acid and sodium tungstate are preferably employed at a molar ratio of phosphorus to tungsten in the range of from 1:2 to 10:1, preferably from 4:1 to 8:1. The heteropolytungstate reacts with hydrogen peroxide in the liquid reaction mixture to form peroxotungstates and peroxotungstophosphates, for example $PO_4[WO(O_2)_2]_4^{3-}$ and $HPO_4[WO(O_2)_2]_2^{2-}$ as well as partially protonated forms thereof, which are presumably the catalytically active species for oxidizing propene.

The catalyst mixture used in step a) also comprises a phase transfer catalyst. The phase transfer catalyst comprises a cation or a compound which forms a cation in the aqueous phase, whereby the cation can form a salt with a peroxotungstate or heteropolyperoxotungstate, which salt is soluble in the organic phase of the liquid reaction mixture. The phase transfer catalyst preferably comprises a singly-charged cation or a compound which forms a singly-charged cation in the aqueous phase. Suitable as phase transfer catalyst are tertiary amines, tertiary and quaternary ammonium salts, and quaternary phosphonium salts. Suitable counterions for tertiary and quaternary ammonium salts are the anions chloride, bromide, nitrate, sulphate, hydrogen phosphate, dihydrogen phosphate, methyl sulfonate, methyl sulphate and ethyl sulphate. The phase transfer catalyst is preferably used in an amount which results in a molar ratio in the liquid mixture of phase transfer catalyst to tungsten in the range of from 0.2:1 to 3:1 and particularly preferably of from 0.4:1 to 1:1, where the molar ratio refers to the cations or compounds forming cations in the employed phase transfer catalyst and to the employed amount of tungsten.

In a preferred embodiment, the phase transfer catalyst is a tertiary amine or a tertiary or a quaternary ammonium salt which comprises in total at least 12 carbon atoms, preferably from 12 to carbon atoms. Preferred are tetraalkylammonium salts. Suitable tertiary amines are for example dodecyldimethylamine, hexadecyldimethylamine, octadecyldimethylamine, tributylamine and trioctylamine. Suitable tertiary ammonium salts are the protonation products of these teriary amines. Suitable quaternary ammonium salts are for example dodecyltrimethylammonium salts, hexadecyltrimethylammonium salts, octadecyltrimethylammonium salts, methyltributylammonium salts and methyltrioctylammonium salts. More preferably, the phase transfer catalyst comprises a tertiary or quaternary ammonium ion having the structure $R^1R^2R^3NR^{4+}$, wherein $R^1$, $R^2$ and $R^3$ are the same or different and are each selected from alkyl groups having from 8 to 10 carbon atoms and $R^4$ is hydrogen or methyl. Most preferably, the phase transfer catalyst comprises methyltri(octylidecyl)ammonium methylsulfate (CAS No. 2387913-24-6).

In another preferred embodiment, the phase transfer catalyst comprises at least one salt having a tertiary or quaternary ammonium ion of the structure $R^1R^2R^3R^4N^+$, where $R^1$ is a $Y—O(C\!\!=\!\!O)R^5$ group with Y being $CH_2CH_2$, $CH(CH_3)CH_2$ or $CH_2CH(CH_3)$ and $R^5$ being an alkyl group or alkenyl group having 11 to 21 carbon atoms, $R^2$ is hydrogen or an alkyl group having 1 to 4 carbon atoms, and $R^3$ and $R^4$ are each independently $R^1$, an alkyl group having 1 to 4 carbon atoms or $Y—OH$. Preferred are quaternary ammonium salts with methylsulphate as the counterion, where $R^2$ is a methyl group and $R^5$ is a linear alkyl group or alkenyl group. Particularly preferred are the salts $(CH_3)_3N^+CH_2CH_2O(C\!\!=\!\!O)R^5CH_3OSO_3^-$, $(CH_3)_2N^+(CH_2CH_2OH)(CH_2CH_2O(C\!\!=\!\!O)R^5)$ $CH_3OSO_3^-$, $(CH_3)_2N^+(CH_2CH_2O(C\!\!=\!\!O)R^5)_2CH_3OSO_3^-$, $CH_3N^+(CH_2CH_2OH)_2(CH_2CH_2O(C\!\!=\!\!O)R^5)$ $CH_3OSO_3^-$, $CH_3N^+(CH_2CH_2OH)(CH_2CH_2O(C\!\!=\!\!O)R^5)_2CH_3OSO_3^-$, $CH_3N^+(CH_2CH_2O(C\!\!=\!\!O)R^5)_3CH_3OSO_3^-$, $(CH_3)_3N^+CH_2CH(CH_3)O(C\!\!=\!\!O)R^5CH_3OSO_3^-$, $(CH_3)_2N^+(CH_2CH(CH_3)OH)(CH_2CH(CH_3)O(C\!\!=\!\!O)R^5)$ $CH_3OSO_3^-$ and $(CH_3)_2N^+(CH_2CH(CH_3)O(C\!\!=\!\!O)R^5)_2CH_3OSO_3^-$, in which $R^5$ is in each case a linear alkyl group or alkenyl group having 11 to 21 carbon atoms. Most preferred is the salt $(CH_3)_2N^+(CH_2CH(CH_3)O(C\!\!=\!\!O)R^5)_2CH_3OSO_3^-$ in which $R^5$ is an alkyl group or alkenyl group having 11 to 17 carbon atoms. The phase transfer catalysts of this embodiment may be prepared by esterifying ethanolamine, isopropanolamine, diethanolamine, diisopropanolamine, triethanolamine or tri-isopropanolamine with a fatty acid and subsequent quaternization with dimethyl sulphate. These phase transfer catalysts have the advantage that they are readily biodegradable, unlike tetraalkylammonium salts, and can be introduced into a biological treatment plant without further pretreatment. The salts with methylsulphate as anion are also less corrosive than tetraalkylammonium halides.

The reaction of step a) is carried out in a liquid reaction mixture which comprises two liquid phases, an aqueous phase with a maximum apparent pH of 6 and an organic phase. The term "apparent pH" here refers to a value determined by measurement with a glass electrode employing a commercial pH meter calibrated with aqueous buffer solutions of known pH for measuring dilute aqueous solutions. This apparent pH differs from the notional pH, i.e. the negative logarithm of the hydrogen ion activity, by a constant value because the normal potential of the glass electrode in the aqueous phase of the reaction mixture, which comprises hydrogen peroxide and glycols, is different than the normal potential in pure water. The apparent pH of the aqueous phase is preferably maintained in the range from 1.0 to 3.5, particularly preferably in the range from 2.0 to 3.0. The apparent pH can be maintained in this range by addition of acid, preferably sulphuric acid or phosphoric acid, or by addition of base, preferably aqueous sodium hydroxide solution. Adjusting the apparent pH in the preferred range provides high selectivity for 1,2-propanediol and prevents enriching propene oxide in the aqueous phase, which simplifies the subsequent separation of propylene glycols from the aqueous phase.

In the reaction step a) the weight ratio of hydrogen peroxide to water fed to step a) is preferably adjusted while maintaining a molar excess of propene to hydrogen peroxide fed to step a). The weight ratio of hydrogen peroxide to water is preferably varied within the range of from 0.05 to 1.5, more preferably from 0.10 to 0.7 and most preferably from 0.15 to 0.45. The molar ratio of propene to hydrogen peroxide fed to step a) is preferably from 1.1:1 to 10:1, more preferably from 1.2:1 to 4:1.

The reaction is preferably conducted at a temperature in the range of from 50 to 110° C., more preferably 60 to 100° C. and particularly preferably 70 to 90° C. The reaction pressure is preferably higher than the vapor pressure of propene at the reaction temperature to ensure that most of the propene is present in the liquid organic phase of the liquid mixture.

The reaction of step a) can be carried out with or without addition of an organic solvent. The reaction is preferably conducted in the presence of at least one organic solvent having a boiling point of more than 100° C., preferably more than 120° C., which has a solubility in water of less than 250 mg/kg at 20° C. Suitable as solvents are alcohols having one or more hydroxyl groups, ethers, esters, ketones and alkylated aromatic hydrocarbons. Adding a solvent can improve extraction of a salt formed of the heteropolytungstate and the phase transfer catalyst into the organic phase. Preferably the amount of organic solvent is selected to provide a proportion of organic solvent in the organic phase during the reaction in the range of from 10 to 90% by weight.

In a preferred embodiment, the organic solvent comprises an epoxidized fatty acid methyl ester. The epoxidized fatty acid methyl ester can be formed in situ in the reaction mixture of step a) by employing a fatty acid methyl ester with unsaturated fatty acid groups which reacts with hydrogen peroxide to the epoxidized fatty acid methyl ester. Particularly preferred are epoxidized fatty acid methyl esters which comprise fatty acid groups originating from vegetable oils, in particular soybean oil. The epoxidized fatty acid methyl esters have the advantage that they have low solubility in the aqueous phase.

In another preferred embodiment, the solvent comprises an alkylated aromatic hydrocarbon having 8 to 12 carbon atoms. Suitable alkylated aromatic hydrocarbons are, for example, 1,2-dimethylbenzene (o-xylene), 1,3-dimethylbenzene (m-xylene), 1,4-dimethylbenzene (p-xylene), ethylbenzene, 1,2,3-trimethylbenzene, 1,2,4-trimethylbenzene, 1,3, 5-trimethylbenzene (mesitylene), 1-ethyl-2-methylbenzene, 1-ethyl-3-methylbenzene and 1-ethyl-4-methylbenzene and n-propylbenzene. Preferably, hydrocarbon mixtures comprising more than 50% by weight, particularly preferably more than 80% by weight, of alkylated aromatic hydrocarbons having 8 to 12 carbon atoms are used as solvent. The use of these solvents enables extracting most of the peroxotungstates into the organic phase of the reaction mixture and recycling them, which allows for operating the process without a need for recovering heteropolytungstate from the aqueous phase of the reaction mixture of step a). The phase transfer catalyst, the molar ratio of phase transfer catalyst to heteropolytungstate, the molar ratio of heteroatom of the heteropolytungstate to tungsten, the molar ratio of propene to hydrogen peroxide and the amount of solvent are then preferably selected to transfer as much as possible of the tungsten present in the liquid reaction mixture into the organic phase.

The phase transfer catalyst, the heteropolytungstate and the optionally used solvent can be added in step a) of the method of the present invention separately or in the form of mixtures containing two or all three of these components. Preferably, a solvent is used in step a) and the phase transfer catalyst and the heteropolytungstate are added dissolved in an organic phase comprising the solvent.

The reaction of step a) may be carried out in the presence of phosphoric acid. Phosphoric acid may be used to provide an apparent pH of the aqueous phase ($P_a$) of the reaction mixture of from 1.0 to 3.5, preferably of from 2.0 to 3.0. The concentration of phosphoric acid and phosphates in the aqueous phase ($P_a$) of the reaction mixture is preferably from 0.2 to 0.8% by weight, calculated as $PO_4^{3-}$ relative to the mass of the aqueous phase. Phosphoric acid may also be present from in situ formation of a polytungstophosphate in the aqueous phase ($P_a$) of the reaction mixture as described above.

The reaction of step a) may be carried out in batch or continuously, with a continuous reaction being preferred. The concentration of hydrogen peroxide in the aqueous phase is preferably maintained in the range of 0.1 to 5% by weight, particularly preferably 0.5 to 3% by weight. The concentration of hydrogen peroxide can be adjusted in this range by appropriate selection of the reaction temperature, the molar ratio of propene to hydrogen peroxide and the residence time of the liquid mixture in the reactor in which the reaction takes place. The residence time of the reaction mixture is preferably adjusted to maintain a hydrogen peroxide conversion in the range of from 80 to 99%.

During the reaction, the liquid mixture is preferably mixed in order to generate a large phase interface between the aqueous phase and the organic phase. For this purpose, the reaction is preferably carried out continuously in a loop reactor which has fixed internals in a tubular section and the liquid mixture is passed through the loop reactor at a flow rate which generates a turbulent flow at the internals. Baffles, static mixing elements, structured packings or random packings can be used as internals for this purpose. In combination to these internals or as an alternative, heat exchangers, such as plate heat exchangers or tube bundle heat exchangers, may be used, in which turbulent flow is generated, for example between the plates of a plate heat exchanger or in the tubes of a tube bundle heat exchanger.

Preferably, all or a part of the reaction heat generated in step a) is removed while the reaction proceeds, preferably by cooling the reaction mixture in a heat exchanger. More preferably, the reaction is carried out continuously in a loop reactor which comprises a heat exchanger within the reactor loop for cooling the reaction mixture.

In step b) of the method of the present invention, the liquid reaction mixture provided by step a) is separated into an aqueous phase ($P_a$) comprising 1,2-propanediol and formic acid and an organic phase ($P_o$). The separation of the two-phase reaction mixture provided by step a) is preferably carried out in a settler vessel. The two-phase reaction mixture is preferably passed through a coalescer element comprising a structured packing or a random packing with a surface wetted by the dispersed phase of the two-phase mixture in order to achieve a more complete separation.

The aqueous phase ($P_a$) typically comprises water, unreacted hydrogen peroxide and the reaction product 1,2-propanediol. The aqueous phase typically also contains dipropylene glycol and tripropylene glycol as well as reaction byproducts, such as 1-hydroperoxy-2-propanol and 2-hydroperoxy-1-propanol formed by reaction of propene oxide with hydrogen peroxide, and formic acid, acetic acid and hydroxyacetone formed by further oxidation of 1,2-propanediol. The aqueous phase may also comprise phosphoric acid and may further contain sodium salts of phosphoric acid if a polytungstophosphate generated in situ by combining phosphoric acid and sodium tungstate is used in step a). The organic phase ($P_o$) comprises unreacted propene and propene oxide that is formed as intermediate when propene is reacted with hydrogen peroxide and has not been hydrolyzed to 1,2-propanediol. The organic phase ($P_o$) typically also comprises one or more salts formed of the heteropolytungstate and the cation of the phase transfer catalyst. The organic phase $P_o$ will also comprise propane, if the propene starting material contains propane, and organic solvent, if an organic solvent having a low solubility in water is used as described further above.

In step c) of the method of the present invention, at least a part of the separated organic phase ($P_o$) is recycled to the reaction step a). Thereby, propene oxide present in the organic phase ($P_o$) is recycled to step a) in order to achieve a complete conversion of propene to 1,2-propanediol, dipropylene glycol and tripropylene glycol. Preferably, the heteropolytungstate present in the organic phase ($P_o$) is recycled into step a), and it is particularly preferred to recycle substantially all of the catalyst mixture that is present in the organic phase into step a).

The organic phase ($P_o$) separated from the liquid reaction mixture provided by step a) may be recycled to step a) without further treatment. If the propene fed to step a) contains propane, it is preferred to separate a stream of unreacted propene from the organic phase in step c) before the organic phase is recycled to step a), with the separated stream of unreacted propene containing as much propane as the impure propene fed to step a). This way, an accumulation of propane in the organic phase of the reaction mixture of step a) can be avoided for a continuous reaction. The separated stream of unreacted propene may be passed to a C3 splitter for separating propene and propane and the recovered propene may be recycled to step a).

The aqueous phase ($P_a$) obtained in step b) is preferably further processed without recycling any part of it directly or indirectly to step a).

In step d) of the method of the present invention, at least a part and preferably all of the aqueous phase ($P_a$) separated in step b) is contacted with a palladium catalyst to provide a treated aqueous phase. Preferably, the aqueous phase ($P_a$) is contacted with the palladium catalyst at a temperature between 0° C. and 200° C., preferably in the range of 100° C. to 180° C. The pressure in contacting step d) is preferably in the range of from 1 to 100 bar and is preferably chosen to maintain a liquid aqueous phase in contacting step d). It is preferred that contacting step d) is performed without adding hydrogen. The aqueous phase ($P_a$) is preferably contacted with the palladium catalyst for a time sufficient to decompose more than 50 mol-% of the formic acid and the amount of catalyst is preferably chosen to provide such level of formic acid decomposition in a time span of from 2 to 90 min.

The palladium catalyst used in step d) may be finely dispersed palladium metal, such as palladium black, or preferably a supported palladium catalyst, which preferably contains palladium metal on a support material selected from activated carbon, $SiO_2$, $TiO_2$, $ZrO_2$, $Al_2O_3$ and aluminium silicates. When a supported palladium catalyst is used, the catalyst preferably comprises from 1 to 5% by weight palladium. Contacting with a supported palladium catalyst may be carried out with a suspended catalyst or with a catalyst fixed bed, preferably in a liquid flooded fixed bed.

In a preferred embodiment, at least a part and preferably all of the aqueous phase ($P_a$) obtained in step b) is subjected to a step f) of catalytic hydrogenation at a temperature of from °C. to 140° C., preferably from 90° C. to 120° C., between steps b) and d) or between steps d) and e). The hydrogenation is preferably carried out using a supported hydrogenation catalyst comprising one or more metals from the group of Ru, Rh, Pt, Ag, Ir, Fe, Cu, Ni and Co on a support, wherein activated carbon, $SiO_2$, $TiO_2$, $ZrO_2$, $Al_2O_3$ and aluminium silicates are preferred as support materials. Preference is given to supported hydrogenation catalysts comprising ruthenium as active metal. The catalytic hydrogenation is preferably carried out at a partial hydrogen pressure of 5 to 50 bar, preferably 5 to 35 bar, more preferred 7 to 30 bar, even more preferred 8 to 25 bar. The hydrogenation catalyst may be used as a suspension or as a fixed bed, a trickle bed hydrogenation with a fixed bed catalyst being preferred. The hydrogenation can prevent problems caused by decomposition of hydrogen peroxide, which has not reacted in step a), in step e) of recovering 1,2-propanediol and dipropylene glycol. The hydrogenation also converts the by-products 1-hydroperoxy-2-propanol, 2-hydroperoxy-1-propanol and hydroxyacetone formed in step a) to 1,2-propanediol and thereby improves the yield of 1,2-propanediol. Preferably, step 0 of catalytic hydrogenation is carried out between steps b) and d) to prevent decomposition of hydrogen peroxide or hydroperoxide by-products by the palladium catalyst used in step d).

In step e) of the method of the present invention, 1,2-propanediol is recovered from the heat treated and optionally hydrogenated aqueous phase ($P_a$), preferably by distillation. Preferably, 1,2-propanediol and higher propylene glycols, like dipropylene glycol and tripropylene glycol, are recovered by a sequence of distillation steps, such as a multi-step distillation with the first distillation step and optionally further distillation steps providing an overhead product comprising water and a bottoms product which is passed to the next distillation step, and a distillation step providing an overhead product comprising 1,2-propanediol and a residuals bottoms product which is preferably subjected to at least one further distillation step. Most preferably, a sequence of distillation steps as described in Ullmann's Encyclopedia of Industrial Chemistry, online edition, entry "Propanediols", page 4, DOI 10.1002/14356007.a22_163.pub2 is used where an overhead product comprising water is separated from a bottoms product comprising 1,2-propanediol and higher propylene glycols in a series of two to four heat integrated distillation steps, followed by a vacuum distillation step which provides 1,2-propanediol as the overhead product and a bottoms product containing higher boiling organic compounds and salts. From this bottoms product, dipropylene glycol and tripropylene glycol may be recovered as overhead products in further vacuum distillation steps. In a preferred embodiment, the heated aqueous phase obtained in step d) is directly fed to a distillation step where an overhead product comprising water is separated in order to use the heat supplied in step d) for recovering 1,2-propanediol in step e).

Contacting all or a part of the separated aqueous phase ($P_a$) with a palladium catalyst prior to recovering 1,2-propanediol reduces the content of formic acid in the aqueous phase, which prevents corrosion by formic acid in step e) of recovering 1,2-propanediol.

The present invention will now be explained in more detail with reference to the examples.

EXAMPLES

Example 1

Preparation of Initial Epoxidation Catalyst Solution

A mixture of 33 g 70% by weight hydrogen peroxide, 155 g demineralized water, 88 g % by weight phosphoric acid and 56 g sodium tungstate dihydrate was stirred for 2 h at room temperature. Then, a solution of 150 g of methyltri (octyl/decyl)ammonium methylsulfate (CAS No. 2387913-

24-6) in 1020 g Hydrosol A 200 ND (a mixture of C10 alkyl benzenes) was added and the mixture was stirred for another 2 h at room temperature. The aqueous and organic phases were then separated to provide 1147 g of organic phase as initial epoxidation catalyst solution.

Reaction of Propene with Hydrogen Peroxide

The reaction of propene with hydrogen peroxide was carried out at a temperature of 80° C. and a pressure of 30 bar in a loop reactor with a loop volume of 0.45 l, a circulation pump and a heat exchanger for adjusting the reaction temperature, which was operated at a circulation rate of 130 kg h$^{-1}$. The reactor was equipped with a catalyst feed reservoir and feed pumps for feeding liquid propene, liquid propane, an aqueous hydrogen peroxide solution and liquid from the catalyst feed reservoir. The initial epoxidation catalyst solution was charged to the catalyst feed reservoir. The loop initially contained reaction mixture from a previous experiment. Circulation was started and maintained at 130 kg h$^{-1}$ and the circulating mixture was heated to 80° C. Then 80 g h$^{-1}$ of propene, 50 g h$^{-1}$ of propane, 210 g h$^{-1}$ of a 15% by weight aqueous hydrogen peroxide solution containing 0.3% by weight phosphoric acid, and 320 g h$^{-1}$ of organic catalyst solution from the catalyst feed reservoir were introduced into the loop reactor, cooling the circulating mixture to maintain a reaction temperature of 80° C. A two-phase oxidation reaction mixture was removed from the loop reactor in an amount corresponding to the amounts added. Phases were separated and 0.2% by weight sodium sulfate was added to the depressurized and cooled aqueous phase to coagulate emulsified organic phase. A second phase separation was carried out after coagulation of the emulsified organic phase. The combined organic phases were passed to the catalyst feed reservoir after depressurizing and cooling to 25° C. After about 11 h of operation, the feeding of reactants and the circulation in the loop reactor were stopped. The next day, circulation in the loop reactor was restarted, dosing of reactants was resumed after the reaction temperature had been established in the loop reactor and the reaction was continued for another 11 h. Aqueous phase for further hydrogenation and contacting with palladium catalyst was collected after a stationary operating state was reached.

Hydrogenation of the separated aqueous phase.

800 g of the aqueous phase separated from the reaction mixture of reacting propene with hydrogen peroxide were charged to a 1 l spinning basket autoclave containing 75 g of a 2% by weight ruthenium on activated carbon supported catalyst in the spinning basket. The autoclave was flushed with nitrogen followed by hydrogen and hydrogenation was carried out at 90° C. and 1.6 MPa hydrogen pressure for 6 h with the basket spinning.

Contacting of the hydrogenated aqueous phase with the palladium catalyst.

50 g of the hydrogenated aqueous phase were added to a 300 ml spinning basket autoclave containing 0.5 g of a 2% by weight palladium on alumina supported catalyst in the spinning basket. After flushing with nitrogen, the autoclave content was heated to 160° C. with the basket spinning and held at this temperature for 60 min at a nitrogen pressure of 15 bar. The autoclave was then cooled to ambient temperature and depressurized.

The aqueous phase was analyzed for formate by ion chromatography with a conductivity detector (Metrohm A Supp 5-250 column (polyvinyl alcohol with quaternary ammonium groups), 0.5 ml/min aqueous eluent with 1 mmol/l NaHCO$_3$ and 3.2 mmol/l Na$_2$CO$_3$, aqueous suppressor regenerant with 100 mmol/I sulfuric acid and 20 mmol/1 oxalic acid) prior to and after the treatment with the palladium catalyst. The ion chromatograms showed that the contacting with the palladium catalyst decreased the area of the peak associated to formate to 49.5% of the area prior to the contacting, which demonstrates decomposition of about half of the formic acid.

Example 2

Example 1 was repeated with the difference that the temperature of contacting with the palladium catalyst was lowered from 160° C. to room temperature (about 23° C.). The ion chromatograms showed that the contacting with the palladium catalyst decreased the area of the peak associated to formate to 70.6% of the area prior to the contacting, which demonstrates that formic acid can also be decomposed at low temperature.

The invention claimed is:

1. A method for the preparation of 1,2-propanediol, comprising:
   a) reacting propene with hydrogen peroxide in the presence of a catalyst mixture comprising a phase transfer catalyst, phosphoric acid, and a heteropolytungstate, in a liquid reaction mixture comprising an aqueous phase with a maximum apparent pH of 6 and an organic phase, wherein apparent pH refers to a value determined by measurement with a glass electrode employing a commercial pH meter calibrated with aqueous buffer solutions of known pH for measuring dilute aqueous solutions;
   b) separating the liquid reaction mixture into an aqueous phase (P$_a$) comprising 1,2-propanediol and formic acid, and an organic phase (P$_o$);
   c) recycling at least a part of the organic phase (P$_o$) to a);
   d) contacting at least a part of the aqueous phase (P$_a$) separated in b) with a palladium catalyst to provide a treated aqueous phase, wherein no hydrogen is added in d); and
   e) recovering the 1,2-propanediol from the treated aqueous phase provided in d).

2. The method of claim 1, wherein the contacting in d) is conducted at a pressure sufficient to maintain a liquid aqueous phase.

3. The method of claim 2, wherein the pressure in d) is from 1 to 100 bar.

4. The method of claim 1, wherein a temperature in d) is between 0° C. and 200° C.

5. The method of claim 1, wherein between b) and d) or between d) and e), at least a part of the aqueous phase (P$_a$) is subjected to a catalytic hydrogenation at a temperature in the range of 80° C. to 140° C.

6. The method of claim 1, wherein e) comprises a multistep distillation, with a first distillation step and optionally further distillation steps providing an overhead product comprising water and a bottoms product which is passed to a next distillation step, and a subsequent distillation step providing an overhead product comprising the 1,2-propanediol and a residuals bottoms product.

7. The method of claim 6, wherein the residuals bottoms product is subjected to at least one further distillation step.

8. The method of claim 1, wherein phosphoric acid is present in a), and wherein the heteropolytungstate is a polytungstophosphate.

9. The method of claim 1, wherein the organic phase in a) comprises an organic solvent having a boiling point of more than 100° C. at atmospheric pressure and a solubility in water at 20° C. of less than 250 mg/kg.

10. The method of claim 1, wherein the phase transfer catalyst comprises at least one selected from the group consisting of a tertiary amine, a tertiary ammonium salt, and a quaternary ammonium salt, and wherein the tertiary amine, the tertiary ammonium salt, and the quaternary ammonium salt each comprises in total at least 12 carbon atoms.

11. The method of claim 10, wherein the phase transfer catalyst comprises a tertiary or quaternary ammonium ion having the structure $R^1R^2R^3NR^{4+}$, wherein $R^1$, $R^2$, and $R^3$ are the same or different and are each an alkyl group having from 8 to 10 carbon atoms, and $R^4$ is hydrogen or methyl.

12. The method of claim 11, wherein in d), the formic acid is decomposed.

13. The method of claim 4, wherein the temperature in d) is in the range of 100° C. to 180° C.

14. The method of claim 5, wherein the catalytic hydrogenation is at a temperature in the range of 90° C. to 120° C.

15. The method of claim 9, wherein the organic solvent is an alkylated aromatic hydrocarbon having 8 to 12 carbon atoms.

\* \* \* \* \*